(12) United States Patent
Massie (10) Patent No.: US 7,839,970 B2
(45) Date of Patent: Nov. 23, 2010

(54) DENTAL AND ORTHOPEDIC DENSITOMETRY MODELING SYSTEM AND METHOD

(76) Inventor: Ronald E. Massie, P.O. Box 873, Lake Ozark, MO (US) 65049

( * ) Notice: Subject to any disclaimer, the term of this patent is extended or adjusted under 35 U.S.C. 154(b) by 1296 days.

(21) Appl. No.: 11/224,472

(22) Filed: Sep. 12, 2005

(65) Prior Publication Data

US 2006/0008050 A1    Jan. 12, 2006

Related U.S. Application Data (63) Continuation of application No. 10/351,567, filed on Jan. 24, 2003, now Pat. No. 6,944,262, which is a continuation-in-part of application No. 10/134,153, filed on Apr. 27, 2002, now abandoned, which is a continuation of application No. 09/452,348, filed on Dec. 1, 1999, now Pat. No. 6,381,301.

(51) Int. Cl.
*G01B 15/00* (2006.01)
(52) U.S. Cl. .......................................... 378/54; 378/56
(58) Field of Classification Search ...................... 705/5
See application file for complete search history.

(56) References Cited

U.S. PATENT DOCUMENTS

| | | | |
|---|---|---|---|
| 3,949,229 A | 4/1976 | Albert | |
| 4,104,532 A | 8/1978 | Weiss | |
| 4,188,537 A | 2/1980 | Franke | |
| 4,239,971 A | 12/1980 | Cushman | |
| 4,259,853 A | 4/1981 | Fleissner | |
| 4,628,356 A | 12/1986 | Spillman | |
| 4,783,793 A | 11/1988 | Virta et al. | |
| 4,813,060 A | 3/1989 | Heubeck et al. | |
| 4,823,369 A | 4/1989 | Guenther et al. | |
| 4,856,038 A | 8/1989 | Guenther et al. | |
| 4,941,164 A * | 7/1990 | Schuller et al. | 378/205 |

(Continued)

FOREIGN PATENT DOCUMENTS

CA    2390334    11/2008

(Continued)

OTHER PUBLICATIONS

Tissue-Integrated Prostheses, Oseointegration in Clinical Dentistry, Edited by Ingvar Branemark, MD., Ph.D. et al., Quintessence Publishing Co., Inc. 1995, pp. 11-70.

(Continued)

*Primary Examiner*—Hoon Song
(74) *Attorney, Agent, or Firm*—Law Office of Mark Brown, LLC (57) ABSTRACT

A dental or orthopedic densitometry modeling system includes a computer with a digital memory adapted for storing patient densitometry information, an input and an output. A dental or orthopedic input device includes energy source and an energy sensor, both of which can be either external or intraoral to the patient. The sensor transfers densitometry signals to the computer, which creates, stores and compares digital densitometry models. A densitometry modeling method includes the steps of creating a densitometry database consisting of dental or orthopedic information and obtaining current dental or orthopedic densitometry information from a patient. The current information is compared to the database, which can include the patient's previous densitometry models, and an updated patient densitometry model is created.

4 Claims, 11 Drawing Sheets

U.S. PATENT DOCUMENTS

| | | | |
|---|---|---|---|
| 5,093,852 A | | 3/1992 | Nishikawa et al. |
| 5,195,114 A | | 3/1993 | Sairenji et al. |
| 5,214,686 A | | 5/1993 | Webber |
| 5,306,306 A | | 4/1994 | Bisek et al. |
| 5,335,260 A | | 8/1994 | Arnold |
| 5,480,439 A | | 1/1996 | Bisek et al. |
| 5,503,559 A | | 4/1996 | Vari |
| 5,528,645 A | | 6/1996 | Koivisto |
| 5,533,080 A | | 7/1996 | Pelc |
| 5,579,361 A | | 11/1996 | Augais et al. |
| RE35,423 E | | 1/1997 | Adams et al. |
| 5,677,940 A | | 10/1997 | Suzuki et al. |
| 5,784,429 A | | 7/1998 | Arai |
| 5,785,041 A | | 7/1998 | Weinstein et al. |
| 5,793,837 A | | 8/1998 | Mezhinsky et al. |
| 5,828,720 A | | 10/1998 | Syrjanen |
| 5,828,721 A | | 10/1998 | Schulze-Ganzlin et al. |
| 5,828,722 A | | 10/1998 | Ploetz et al. |
| 5,835,555 A | | 11/1998 | Barry et al. |
| 5,836,876 A | * | 11/1998 | Dimarogonas ............ 600/407 |
| 5,838,765 A | | 11/1998 | Gershman |
| RE36,132 E | | 3/1999 | Bisek et al. |
| RE36,162 E | | 3/1999 | Bisek et al. |
| 5,917,882 A | | 6/1999 | Khutoryansky et al. |
| 5,917,883 A | | 6/1999 | Khutoryansky et al. |
| 5,930,327 A | | 7/1999 | Lin |
| 5,995,583 A | | 11/1999 | Schick et al. |
| 6,038,287 A | | 3/2000 | Miles |
| 6,069,935 A | | 5/2000 | Schick et al. |
| 6,381,301 B1 | | 4/2002 | Massie |
| 6,385,283 B1 | * | 5/2002 | Stein et al. ............ 378/54 |
| 6,405,071 B1 | | 6/2002 | Analoui |
| 6,424,694 B1 | | 7/2002 | Molteni |
| 6,496,558 B2 | | 12/2002 | Graumann |
| 6,664,986 B1 | | 12/2003 | Kopelman et al. |
| 6,690,761 B2 | | 2/2004 | Kopelman et al. |
| 6,821,116 B2 | | 11/2004 | Severance |
| 7,099,428 B2 | | 8/2006 | Clinthorne et al. |
| 7,203,273 B2 | | 4/2007 | Linnosaari |
| 2002/0114425 A1 | | 8/2002 | Lang et al. |
| 2002/0178032 A1 | * | 11/2002 | Benn et al. ............ 705/2 |
| 2005/0015002 A1 | * | 1/2005 | Dixon et al. ............ 600/407 |

FOREIGN PATENT DOCUMENTS

| | | |
|---|---|---|
| EP | 0180482 | 5/1986 |
| EP | 0314506 A1 | 5/1989 |
| EP | 0652433 | 5/1995 |
| EP | 1237483 | 11/2008 |
| WO | WO9311707 | 6/1993 |
| WO | WO-0138824 | 5/2001 |
| WO | WO 01/39667 | 6/2001 |

OTHER PUBLICATIONS

A. Boyde, R. Travers, F.H. Glorieux, S. J. Jones, The Mineralization Density of Iliac Crest Bone From Children with Osteogenesis Imperfecta, Calcified Tissue International, Vaolume 64 Issue 3, Mar. 1999, p. 185-190.

"Written Opinion of the ISA", PCT/US/04/01825, Feb. 25, 2005.

"Supplemental European Search Report", *Massie Application No. 04704878.0*, PCT/US2004001825, Jun. 10, 2008.

"Notice of Reason for Rejection", Japan Patent Application No. 2006-502953 based on PCT/US2004/001825, Aug. 3, 2009.

"Notice of Reason for Rejection", Japan Patent Application No. 2001-541403 based on PCT/US00/32905, (Nov. 24, 2009).

Krennmair, Gerald, MD et al., "Maxillary Sinus Aspergillosis: Diagnosis and Differentiation of the Pathogenesis Based on Computed Tomography Densitometry of Sinus Concretions", American Association of Oral and Maxillofacial Surgeons, (1995), 657-663.

Elsasser, Urs, P., et al., "Bone Density Measurement with Computed Tomography", *British Medical Bulletin* vol. 36, No. 3, (1980), 293-296.

Exner, G., M., et al., "Bone Densitometry Using Computed Tomography", *British Journal of Radiology*, vol. 52, (1979), 14-23.

"International Search Report", PCT/US00/32905, (Jan. 26, 2001).

"Final Decision for Rejection", Japan Patent Application No. 2006-502953.

"Notice of Reason for Rejection", Japan Appl. No. 2001-541403 corresponding to PCT/US00/32905.

* cited by examiner

DENTAL AND ORTHOPEDIC DENSITOMETRY MODELING SYSTEM AND METHOD

CROSS-REFERENCE TO RELATED APPLICATIONS

This application is a continuation of Ser. No. 10/351,567, filed Jan. 24, 2003 now U.S. Pat. No. 6,944,262, which is a continuation-in-part of Ser. No. 10/134,153, filed Apr. 27, 2002 now abandoned, which is a continuation of Ser. No. 09/452,348, filed Dec. 1, 1999, now U.S. Pat. No. 6,381,301 B1, in which priority is claimed and which are incorporated herein by reference.

BACKGROUND OF THE INVENTION

1. Field of the Invention

The present invention relates generally to dental and orthopedic diagnosis, forensics, identification, biometrics and treatment, and in particular to a densitometry modeling system and method.

2. Description of the Related Art

The field of dental diagnostics is generally concerned with locating pathologies in the dental structure, i.e. the teeth and the surrounding tissue and bone. Three of the most common pathologies are: 1) caries associated with decay; 2) fractures; and 3) apical abscesses. The system and method of the present invention are primarily, but not exclusively, concerned with detecting these pathologies and with orthopedics.

Early detection of dental pathologies is very important in minimizing damage. Conventional diagnosis procedures are generally performed using dental X-rays (both fixed beam and scanning beam), explorers, and other conventional equipment.

Incipient caries, particularly those located within the enamel surface, often go undetected with conventional equipment. When such caries are finally found, considerable damage to tooth structure may have already occurred. Subsurface, incipient caries are located entirely within the enamel layer of the teeth. They are particularly difficult to locate using conventional diagnostic equipment and procedures. By the time such incipient caries are located, the extent of the damage is often 17% to 23% greater than it would appear to be on a conventional X-ray negative.

Dental fractures can result from bruxism (teeth grinding), trauma, etc. The dental structure that has been weakened by various causes, such as decalcification, is particularly susceptible to fractures. Fractures can assume various configurations, including "craize", vertical, oblique and horizontal line patterns. Fracture patterns and configurations can be particularly difficult to locate using conventional X-ray equipment and procedures. For example, fractures which are generally parallel to the X-ray beam are often undetectable on an X-ray negative. Undetected, and hence untreated, fractures can provide direct paths through the enamel layer of the teeth whereby bacteria can invade the dentin and pulp layers. Pathologies in the dentin and pulp layers are often associated with considerable pain and tooth loss.

Apical abscesses comprise yet another dental condition which can be difficult to diagnose with conventional equipment, particularly in the early stages. Advanced apical abscesses can cause considerable pain because they involve the neurovascular bundles located in the root canals as well as the osseous tissue around the apex of the root. Early detection of apical abscesses can lead to appropriate, early-stage treatment, thus avoiding advanced disease processes with resultant pain, swelling, and other serious health consequences and complications.

Tomography or sectional radiography techniques using scanning X-ray beams have previously been employed for dental applications. For example, U.S. Pat. Nos. 4,188,537; 4,259,583; 4,823,369; 4,856,038; and 5,214,686 all relate to dental X-ray diagnosis utilizing scanning techniques and are incorporated herein by reference.

In the medical field, densitometry procedures are used for measuring bone morphology density (BMD) by utilizing scanning X-ray beam techniques. Examples are shown in U.S. Pat. Nos. 5,533,080; 5,838,765; and U.S. Pat. No. Re. 36,162, which are incorporated herein by reference. Medical applications of densitometry include the diagnosis and treatment of such bone diseases as osteoporosis.

The availability of relatively fast computers with large memories at reasonable costs has led to the digitalization of X-ray images for mapping BMD models in various formats. For example, BMD images use color to identify varying densities. Digital BMD patient models are also used for comparison purposes with standard models and with patients' own prior BMD histories. Age correction factors can be applied to patients' models for diagnosing and monitoring the onset and progress of such medical conditions as osteoporosis and the like. The present invention utilizes such densitometry modeling and mapping techniques for dental applications.

In addition to pathology detection and diagnosis, the present invention has applications in monitoring osseointegration. Osseointegration occurs at the interface between bone structures and prostheses, such as implants and replacement joints. For example, dental implants osseointegrate with patients' dental structure. The application of tomographical densitometry techniques to osseointegration monitoring can provide the dental or medical practitioner with important information in evaluating the effectiveness of implant procedures.

Heretofore there has not been available a system or method for applying the technology of densitometry to dental and medical applications such as the detection of caries and decalcification and the monitoring of osseointegration in connection with dental and medical prostheses.

SUMMARY OF THE INVENTION

In the practice of the present invention, a dental and orthopedic densitometry modeling system utilizes a controller with a microprocessor and a and in a different memory. An input device inputs data to the microprocessor for controlling the operation of the modeling system and for providing a database including densitometry parameters for comparison with a patient's densitometry model. The controller controls the operation of X-ray equipment, which is adapted for scanning patients' dental and orthopedic structures along preprogrammed scan paths. The X-ray output is processed by the microprocessor for creating a densitometry model, which can be output in various formats. In the practice of the method of the present invention, a patient and the X-ray equipment are positioned relative to each other. A controller is preprogrammed with a scan path and with data corresponding to the patient. The X-ray equipment emits and detects X-ray beams at first and second energy levels to provide densitometry output. The densitometry output is digitized and merged to provide a tomographic model, which can be compared to predetermined parameters unique to the patient. The model can be output in various formats, including a visual image color-coded to depict varying dental and orthopedic structure densities. Applications of the system and methodology include diagnosis, treatment, identification, forensics and biometrics.

PRINCIPLE OBJECTS AND ADVANTAGES OF THE INVENTION

The principle objects and advantages of the present invention include: providing a dental and orthopedic diagnostic application for densitometry; providing such an application which includes a method for modeling dental and orthopedic structure using densitometry; providing such a method which includes dual-energy, X-ray emission and detection; providing such a method which includes providing a color-coded output model showing dental density; providing such a method which detects incipient caries; providing such a method which is adapted for detecting decalcification beneath the surface of the dental enamel layer; providing such a method which employs scanning X-ray techniques; providing such a method which utilizes commercially available tomography equipment and other equipment as described; providing such a method which detects dental fractures; providing such a method which detects dental apical abscesses; providing such a method which detects dental pathologies at the micron level; providing such a method which facilitates the monitoring of decalcification in dental structures for determining appropriate treatment; providing such a method which is adaptable for monitoring osseointegration; providing such a method which can be practiced with relatively minor changes to existing densitometry equipment; providing such a system and method which have applications in dental and medical diagnosis, treatment, identification, forensics and biometrics; and providing such a system and method which are economical in operation and particularly well adapted for the proposed usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE PREFERRED EMBODIMENTS

I. Introduction and Environment

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

II. Dental Densitometry Modeling System 2

Figure 1:
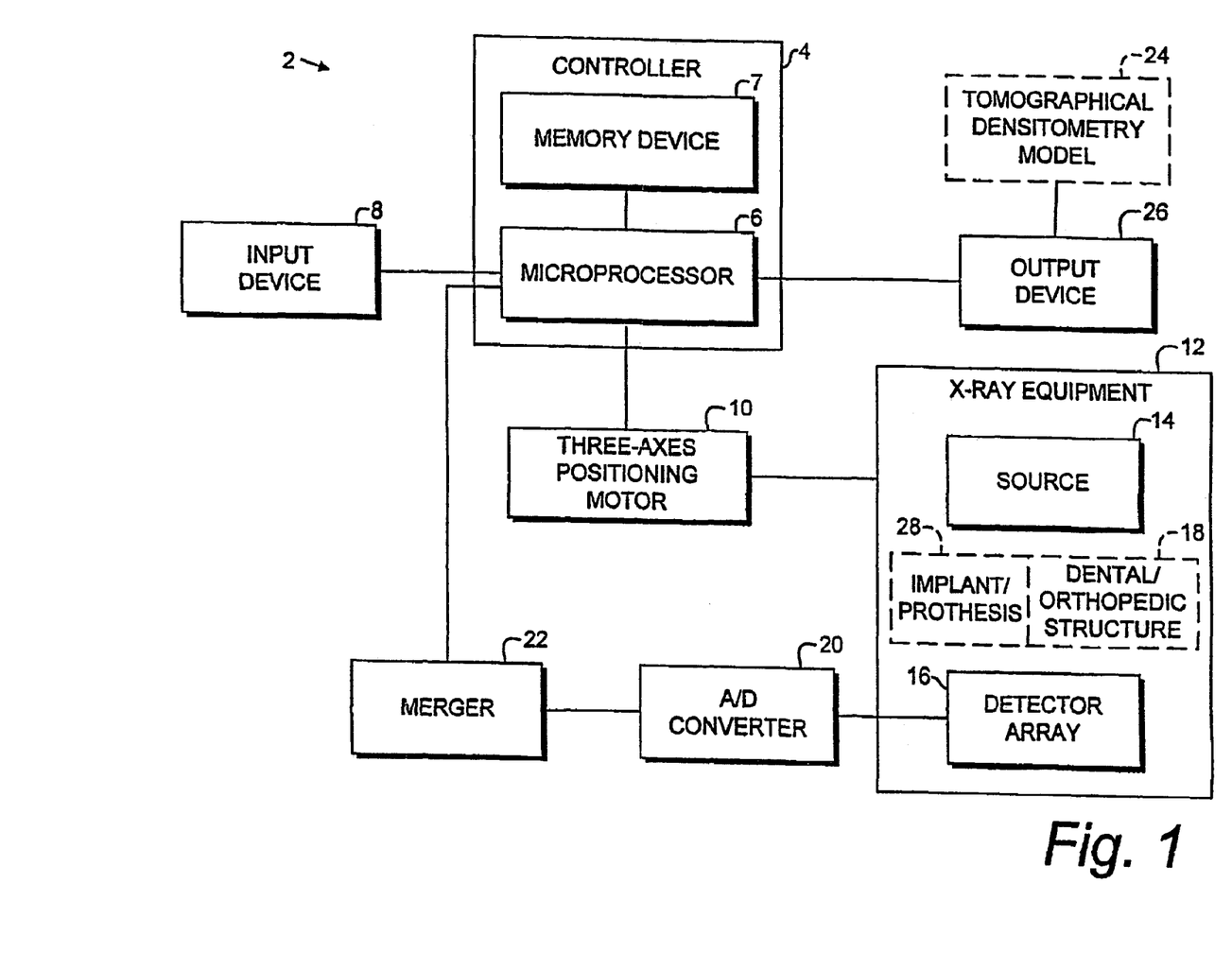
FIG. 1 is a schematic, block diagram of a dental and orthopedic densitometry modeling system embodying the present invention.

Referring to the drawings in more detail, the reference numeral 2 generally designates a dental and orthopedic densitometry modeling system embodying the present invention. The system 2 includes a controller 4 with a microprocessor 6 connected to a digital memory device 7. The hardware components of the controller 4, i.e. the microprocessor 6 and the memory device 7, can comprise any of a number of suitable hardware devices which are commercially available and are suitable for this application. In addition to various programmable logic devices (PLDs) and special-purpose microprocessors, general purpose, commercially available personal computers can be utilized in the controller 4. The controller 4 can be programmed in any suitable manner utilizing any of a variety of commercially available programming languages and software development systems.

The microprocessor 6 is adapted to receive input from one or more input devices 8, such as a keyboard, a pointing device (e.g., a mouse), a communications link, or another computer. Without limitation on the generality of useful data which can be input via the input device(s) 8, such data can include: 1) a patient's dental and orthopedic records, including previous tomographical densitometry models; 2) baseline tomographical densitometry models, which can be adjusted to accommodate for such factors as age, gender, size, weight, etc.; and 3) a preprogrammed scan path for the X-ray equipment.

The microprocessor 6 controls a positioning motor 10 which is operably connected to X-ray equipment 12 and is adapted for moving same through three axes of movement. Examples of X-ray equipment adaptable for use with the present invention are disclosed in U.S. Pat. Nos. 5,533,080; 5,838,765; and U.S. Pat. No. Re. 36,162, which are incorporated herein by reference. The X-ray equipment 12 includes an X-ray beam source 14 and a detector array 16. The X-ray beam can suitably collimated to assume any suitable configuration, such as fan, pencil, cone, etc. With the scanning technique disclosed, a restricted (i.e. collimated) beam is preferred. The source and the detector array 14, 16 are adapted for positioning on either side of a patient's dental/orthopedic structure 18.

Analog signals from the detector array 16 are output to an analog-to-digital (A/D) convertor 20, from which digitized signals are transmitted to a merger device 22 for merging into formats suitable for processing and analyzing by the microprocessor 6. The microprocessor 6, using data from the merger device 22, creates a tomographical densitometry model 24 which is transmitted to an output device or devices 26. Without limitation on the generality of useful output devices 26, it can comprise a monitor, a display, a printer, a communications link, and/or another computer. For example, a color printer can be utilized to provide a color-coded graphical representation of the tomographical densitometry model 24. The color coding can correspond to densities, thus identifying potential problem areas where decalcification has occurred and resulted in lower density. The tomographical densitometry model 24 can also be useful for monitoring osseointegration, since the density of the dental/orthopedic structure 18 (tissue and bone) in the vicinity of an implant 28 or other prostheses can provide an important diagnostic tool for the use of the dental or medical practitioner in assessing the effectiveness of an implant or prosthetic procedure. The tomographical densitometry model 24 is also entered into the computer's memory device 7.

III. Dental and Orthopedic Densitometry Modeling Method

Figure 2:
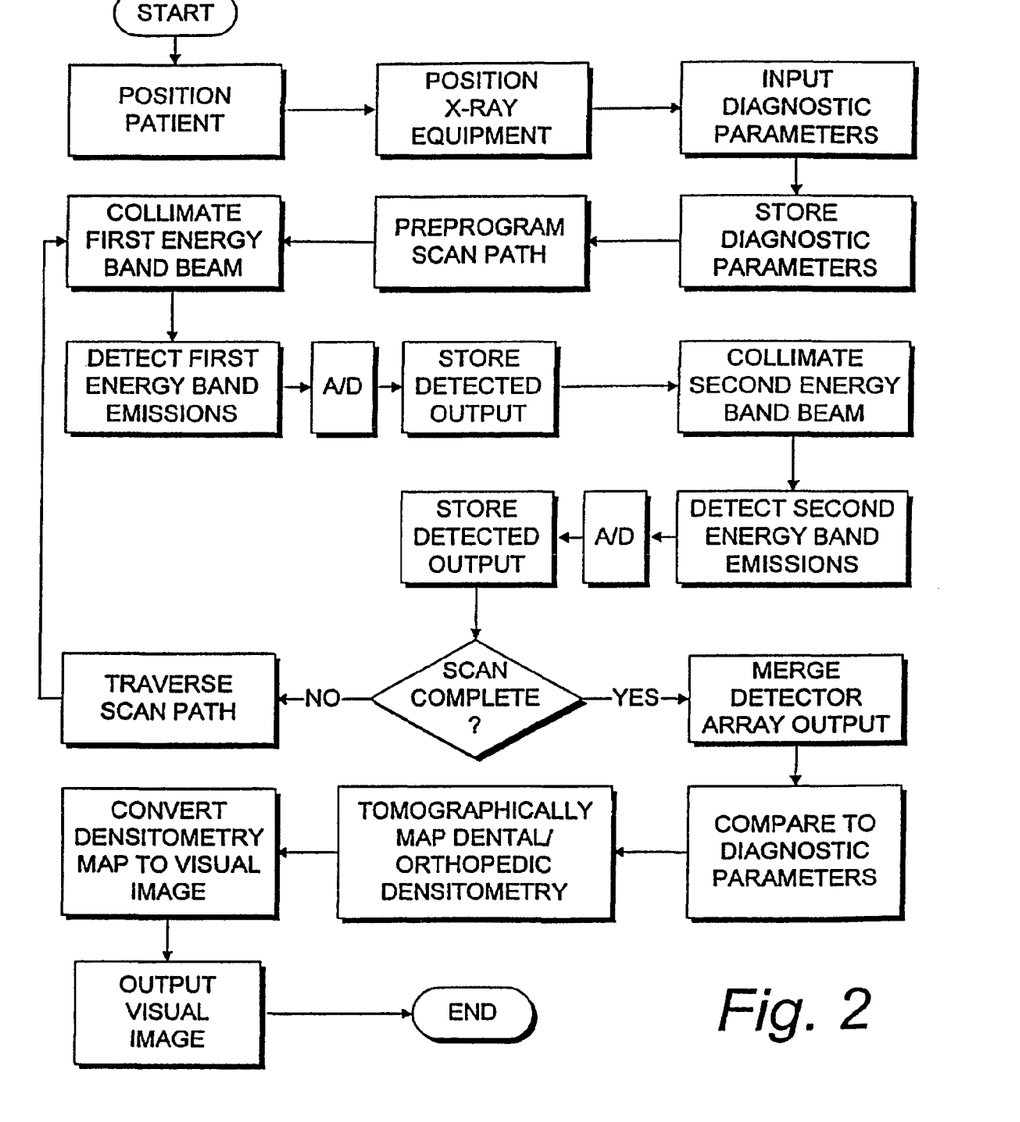
FIG. 2 is a flowchart of a dental and orthopedic densitometry modeling method embodying the present invention.

FIG. 2 is a flow chart of a dental and orthopedic densitometry method embodying the present invention. The method steps include positioning a patient and positioning the X-ray equipment relative to the patient, i.e. with the patient's dental/orthopedic structure to be examined located between the X-ray source 14 and the detector array 16.

Diagnostic parameters are input to the system and can comprise, for example, the patient's prior tomographical densitometry models and standardized models. The tomographical densitometry models can be corrected and/or adjusted to account for patients' age, gender, physical characteristics, etc. The input diagnostic parameters can be stored in the computer's memory device. A scan path for the X-ray equipment is preprogrammed in the computer.

The scanning procedure is commenced by collimating a first energy band beam, detecting emissions from same with a detector array, and converting the analog output of the detector array to a digital signal. The digital signal is output for storage in the computer. The steps of collimating the energy band beam and detecting, digitizing and storing same are repeated for a second energy band beam. The Bisek et al. U.S. Pat. No. Re. 36,362 discloses the use of dual-energy X-ray beams in medical densitometry applications. As discussed therein, dual-energy densitometry can result in a more accurate patient model.

The X-ray equipment then traverses the preprogrammed scan path and the first/second energy band steps are repeated until the scanning procedure is complete. The digitized detector array output is merged and compared to the diagnostic parameters which are stored in the computer's memory. The dental/orthopedic densitometry is tomographically modeled and output, for example to a monitor or printer for converting the model to a visual image. The visual image is output in a visible form for use by dental and medical practitioners.

IV. Modified Embodiment Densitometry Modeling Systems 102

Figure 3:
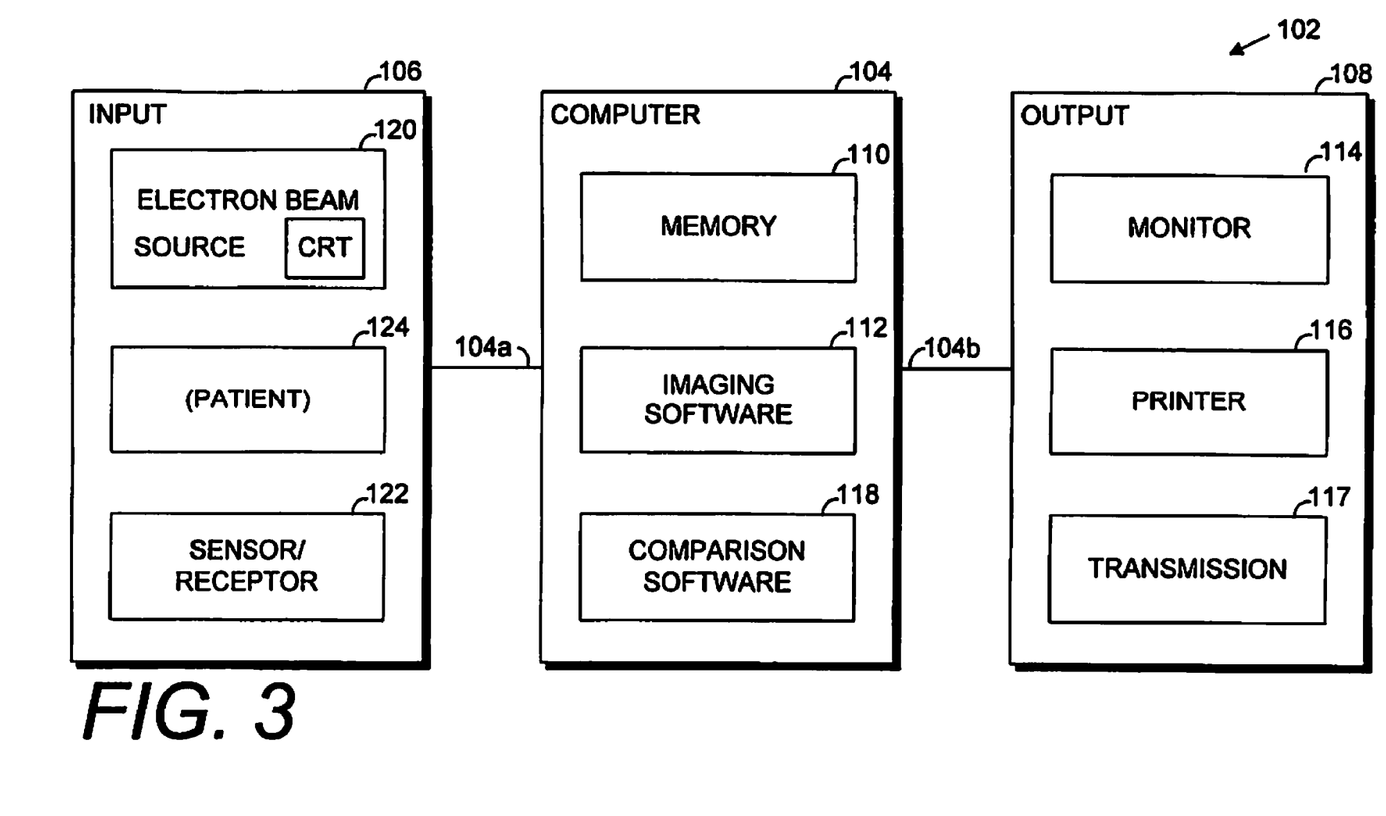
FIG. 3 is a block diagram of a dental or orthopedic densitometry modeling system comprising a first modified embodiment of the present invention.

A densitometry modeling system 102 comprising a first modified embodiment of present invention is shown in FIG. 3 and generally includes a computer 104 with an input 104a and an output 104b. Input and output devices 106 and 108 are connected to the computer input and output 104a,b respectively.

The computer 102 includes a memory 110, such as a hard drive, a tape drive, an integrated circuit (e.g., RAM) or some other suitable digital memory component, which can be either internal or external to the computer 102. Imaging software 112 is provided for converting the digital data into images, which are adapted for visual inspection by displaying same on a monitor 114 or by printing same on a printer 116 of the output device 108. Such images can also be transmitted by a suitable transmission device 117, such as a fax or modem. The computer 104 also includes comparison software 118, which is adapted for digitally comparing baseline and patient-specific dental and orthopedic densitometry models.

The input device 106 includes an electron beam source 120 and a sensor/receptor 122, which are adapted for positioning with at least a portion of the patient 124 therebetween. A wide variety of source and sensor/receptor combinations are included in the scope of the present invention. Preferably the electron beam source 120 emits a collimated electron beam adapted for scanning the patient's dental/orthopedic structure. Such devices can be located internal or external to the patient and include "wands" and "pens". Micro devices are also available that are adapted for mounting on the end of a stylus apparatus. Both hard-wired and wireless (RF) types of source devices can be employed. External devices include electron beam heads mounted on articulated arm assemblies, which are commonly found in dental operatories and other medical workstations. Various hand-held, fixed-position and enclosure-type devices can also provide the electron beam emissions. Control of electron beam source 120 can be automated with the computer 104, or manual in the case of hand-held devices.

The sensor/receptor 122 can likewise be positioned internal or external to the patient. For example, various types of intraoral sensors are available. Phosphorus film sensors are used like X-ray film and are converted and "read" by the computer to transfer the digital data recorded thereon. Other types include charge coupled devices (CCD) and charged metal oxide semiconductor (CMOS) devices, which output digital data from respective circuits associated therewith. Micro printed circuits can be installed on such sensors and provide digital sensor output to the computer input 104a.

Still further, either or both of the beam source 120 and the sensor/receptor 122 can be preprogrammed for computer-controlled movement with respect to the patient 124. Thus, panoramic or tomographic images can be obtained with the patient immobilized. Such equipment is commercial available and typically moves through an arc of approximately 120 degrees for dental applications. The specific electron beam source 120 and sensor/receptor 122 components can be chosen as necessary for the type of model desired. For example, periapical, bite wing, full mouth, panoramic and cephalometric imaging are all widely used in dentistry, oral surgery and related fields. Still further, the system contemplates removable use on and inspection of individual tooth anatomy by use of a wand, pen or similar device adapted for placement intraorally by the dentist. Thus, the densitometry changes with respect to particular "watch" areas can be closely monitored.

Yet another type of electron beam source 120 comprises a miniaturized, hand-held CRT adapted for localized applications. For example, areas deemed susceptible to incipient caries and decay can be diagnosed and identified as "watch" areas, which the dental practitioner would specifically examine with such a miniaturized CRT source device during the course of follow-up office visits and procedures. Thus, patients would be exposed to only minimal levels of radiation in connection with such highly localized and tooth-specific densitometry models. An advantage of the system 102 is that models can be processed and compared nearly instantaneously. Thus, in a single appointment the dentist can obtain, compare and analyze multiple, limited-scope densitometry models specifically directed to areas of concern.

Figure 4A:
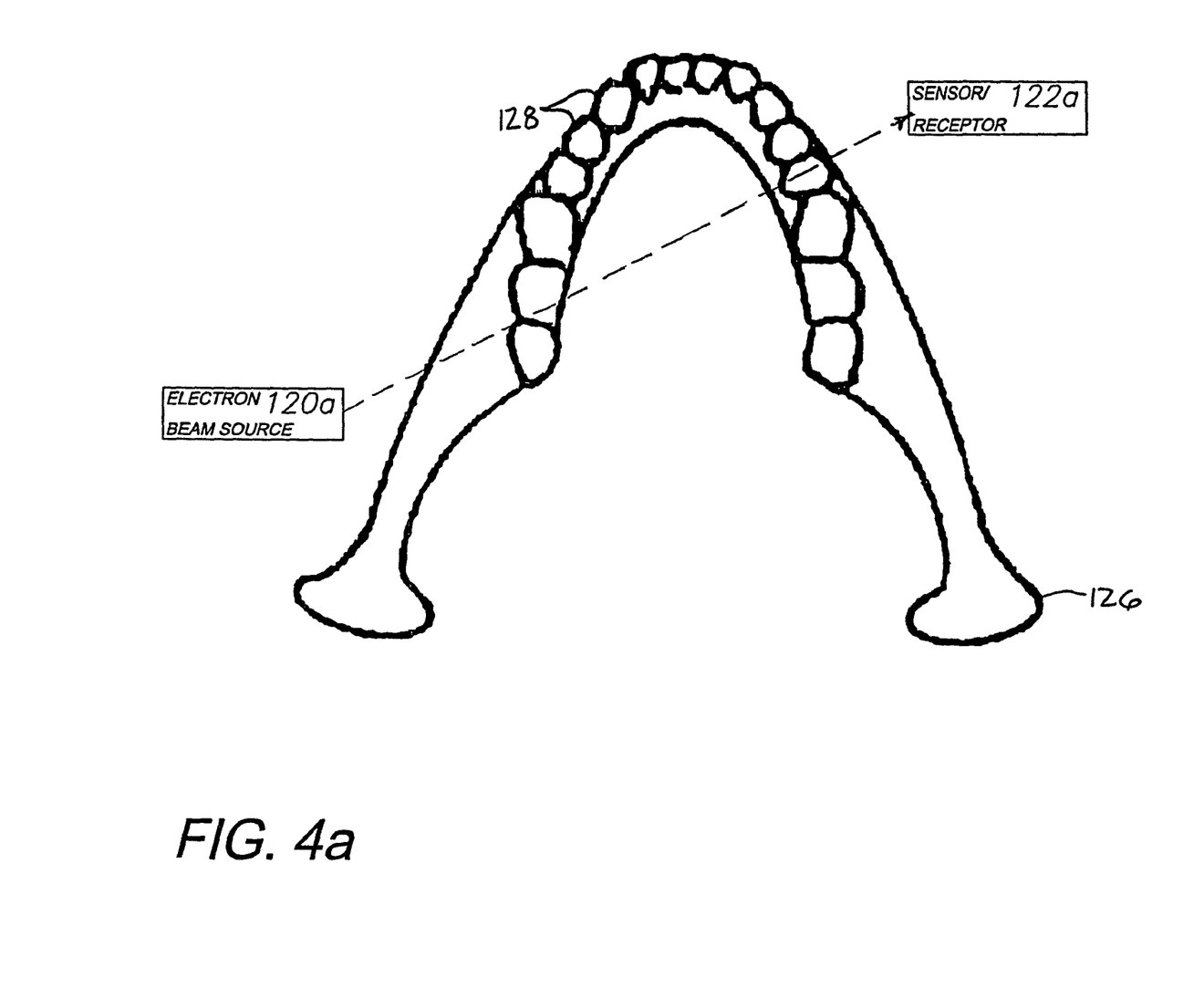
FIG. 4a is diagram of an application with an external electron beam source and an external sensor/receptor.
Figure 4B:
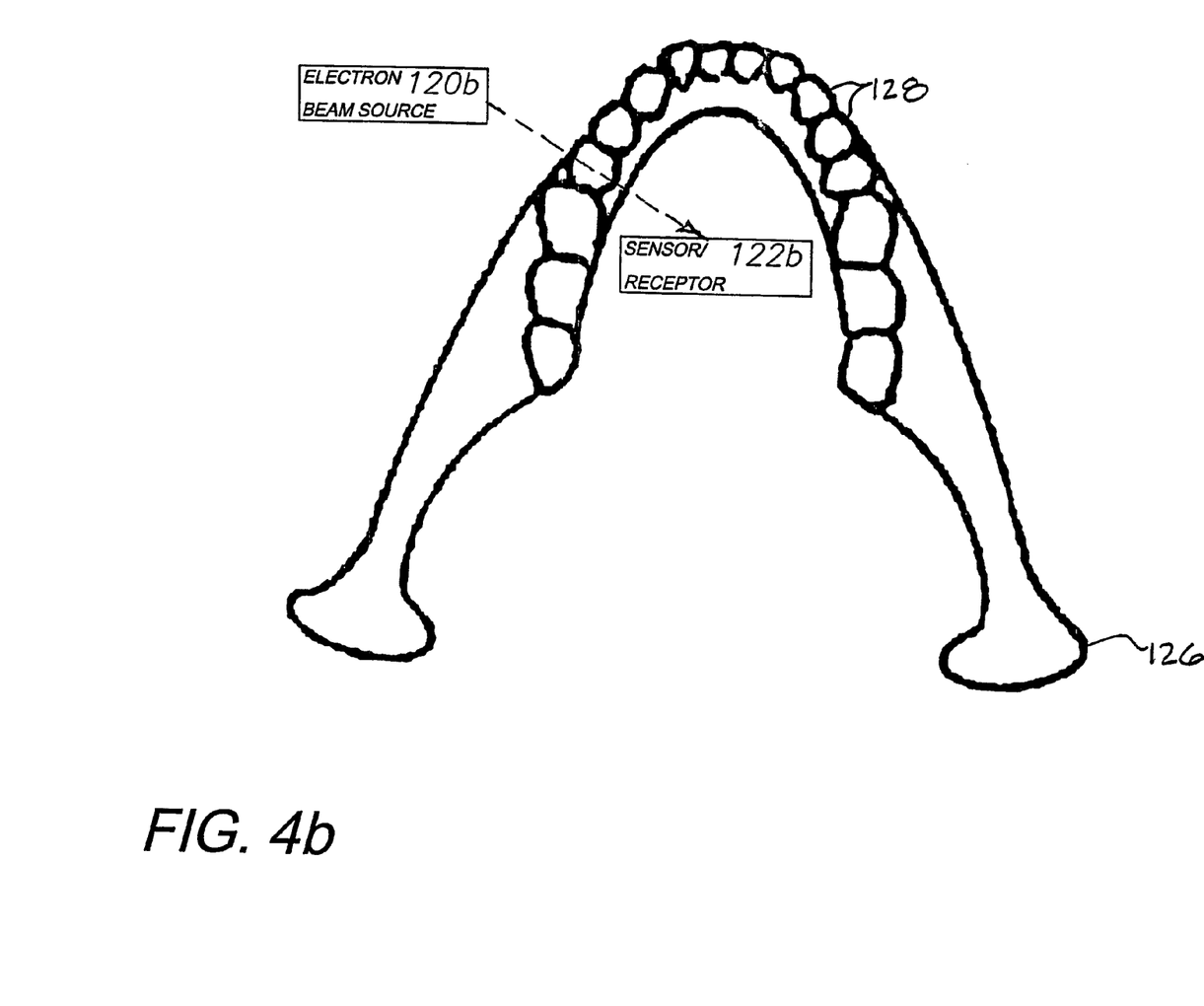
FIG. 4b is a diagram of an application with an external electron beam source and an internal sensor/receptor.
Figure 4C:
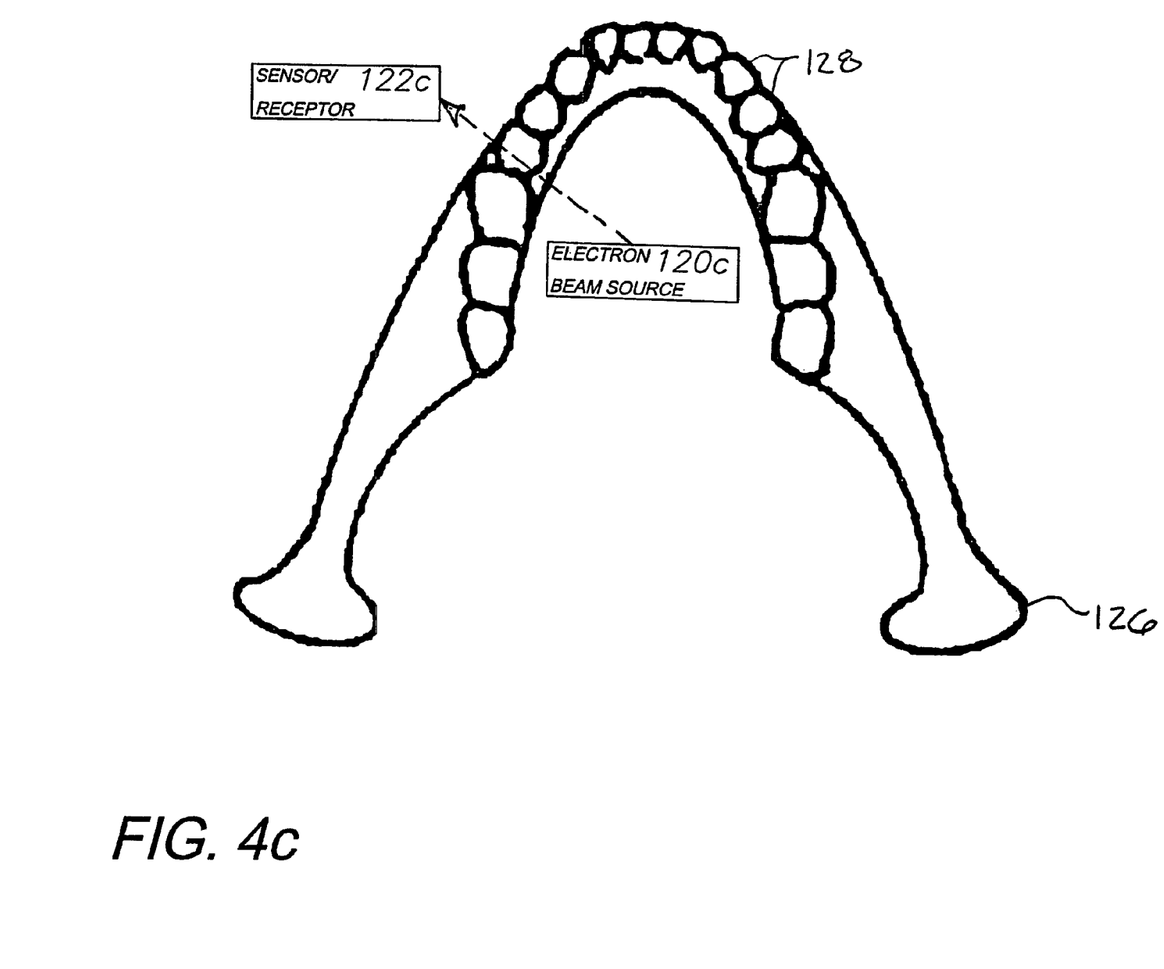
FIG. 4c is a diagram of an application with an internal electron beam source and an external sensor/receptor.
Figure 4D:
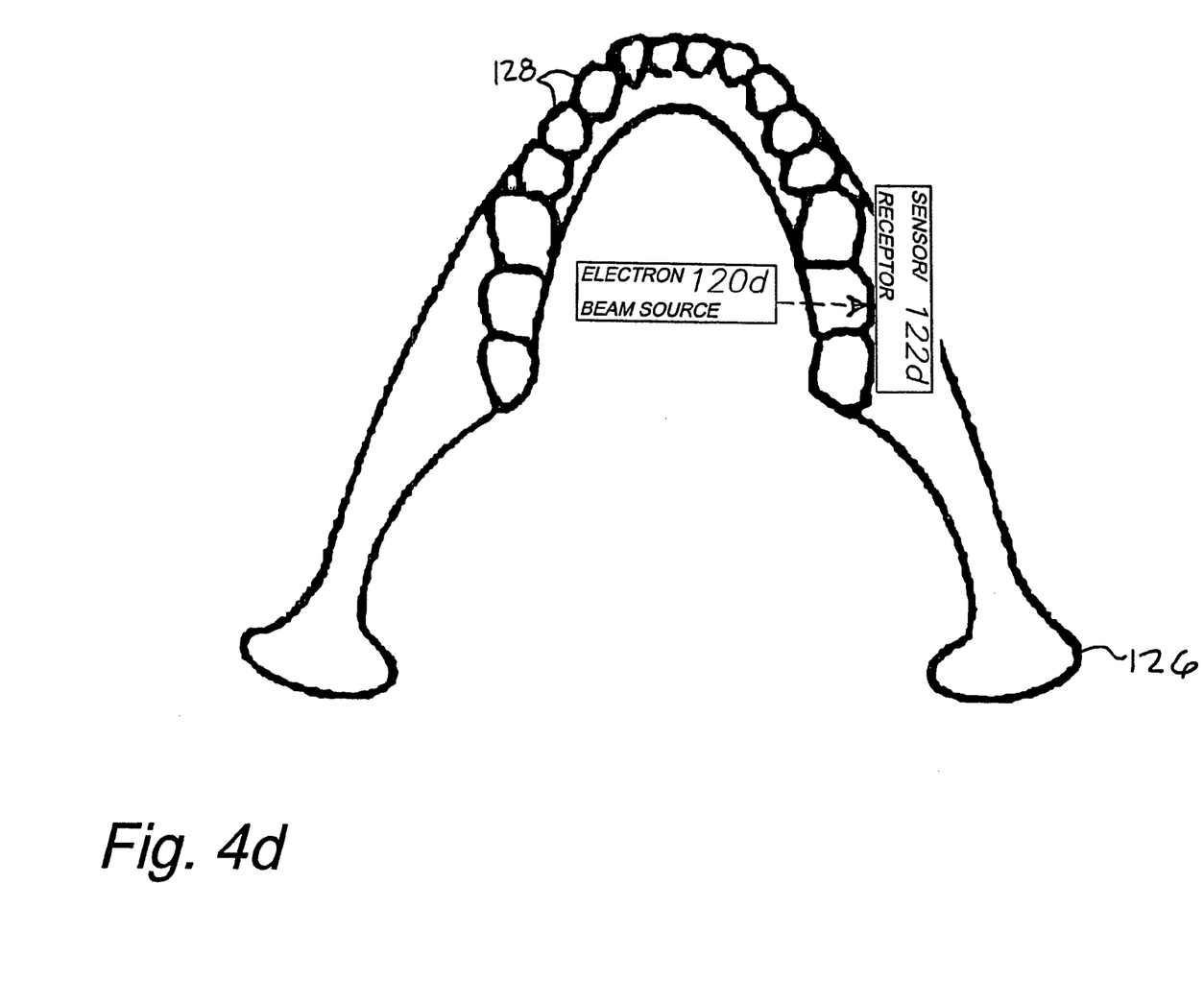
FIG. 4d is a diagram of an application with an internal electron beam source and an internal sensor/receptor.

FIGS. 4a-d show alternative configurations and placements of the electron beam sources 120 and the sensor/receptors 122 with respect to the mandible 126 and teeth 128 of the patient 124. FIG. 4a shows a beam source 120a and a sensor/ receptor 122a both placed externally whereby the electron beam passes through the patient 124. Such configurations can be preprogrammed to travel through predetermined arcs or orbits around the patient 124 in order to compile a panoramic, whole mouth or cephalometric image. FIG. 4b shows an external beam source 120b and an internal sensor/receptor 122b. FIG. 4c shows an internal beam source 120c and an external sensor/receptor 122c. FIG. 4d shows both the beam source 120d and the sensor/receptor 122d positioned intraorally.

V. Modified Densitometry Modeling Methods and Applications

Figure 5:
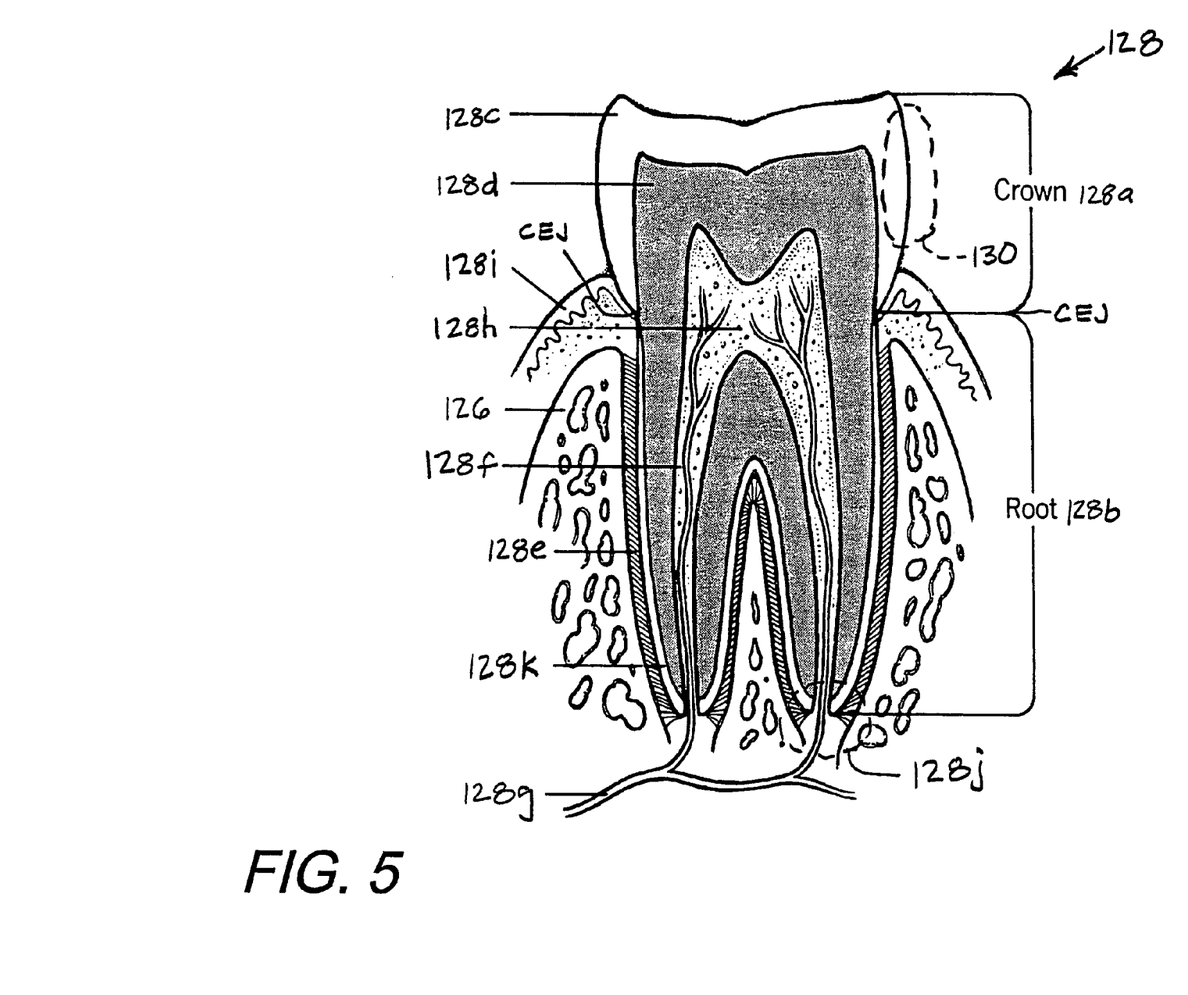
FIG. 5 is a diagram of a tooth structure, showing the locations of particular areas that are suited for densitometry monitoring with the system and method of the present invention.

Without limitation on the generality of useful dental and orthopedic applications of the modeling methods and applications for the present invention, several dental applications are described in detail. FIG. 5 shows a tooth 128 with a crown 128a and a root 128b. The crown 128a includes enamel 128c covering dentin 128d. The root 128b is embedded within a periodontal membrane 128e and includes a root canal 128f through which a neurovascular bundle 128g comprising a nerve, artery and vein passes. The root canal 128f is filled with pulp 128h and surrounded by cementum 128k. The root 128b is embedded in the bone structure of the mandible or the maxilla 126, over which the gingiva and the gingival fibers 128i are located. The cemento-enamel junction (CEJ) is located where the crown 128a meets the root 128b and is the common reference point for periodontal disease. Locations on the crown 128a between the adjacent teeth 130 are common locations for caries because bacteria tend to congregate in such locations unless dislodged by brushing and flossing. Another common problem area is located at the root apex 128j, where abscesses form.

Figure 6A:
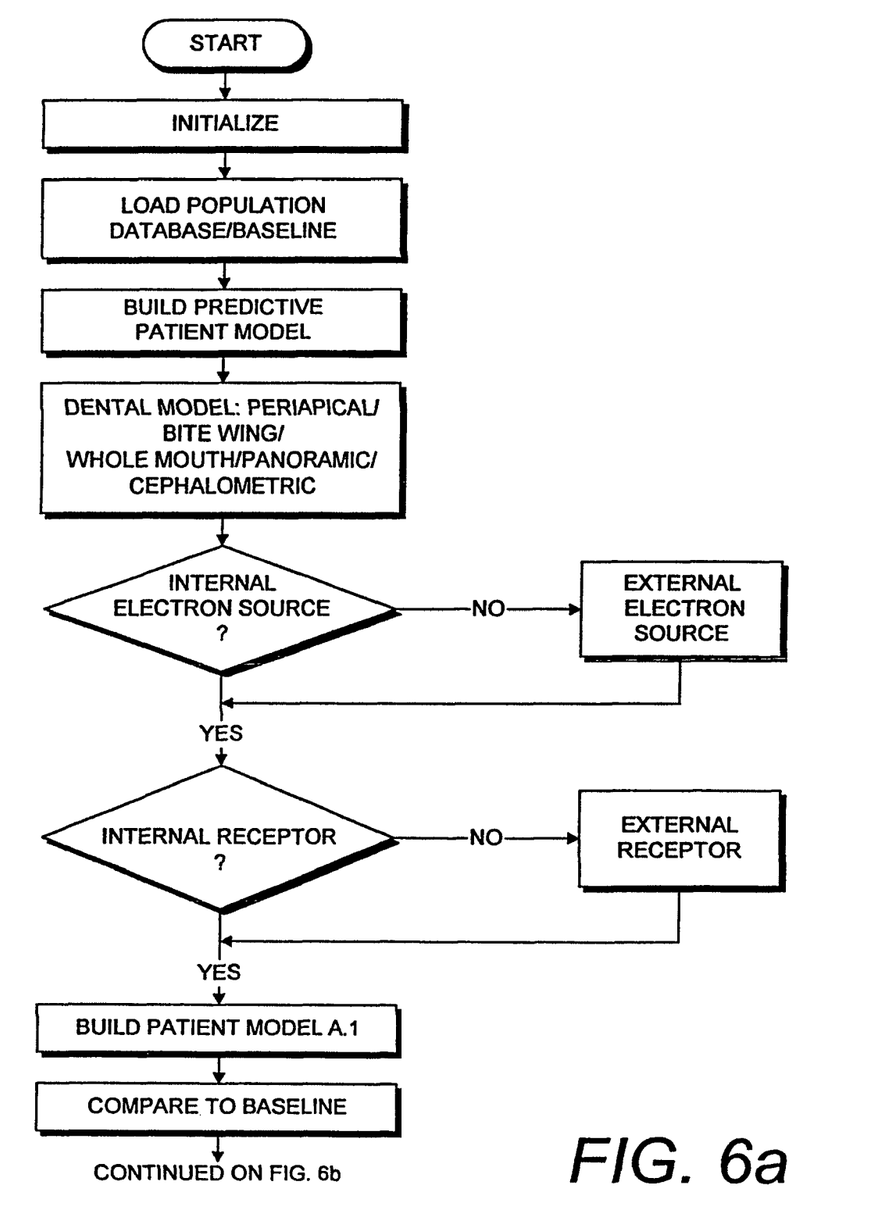
FIGS. 6a,b show a flowchart of a patient-specific densitometry modeling method according to the present invention.
Figure 6B:
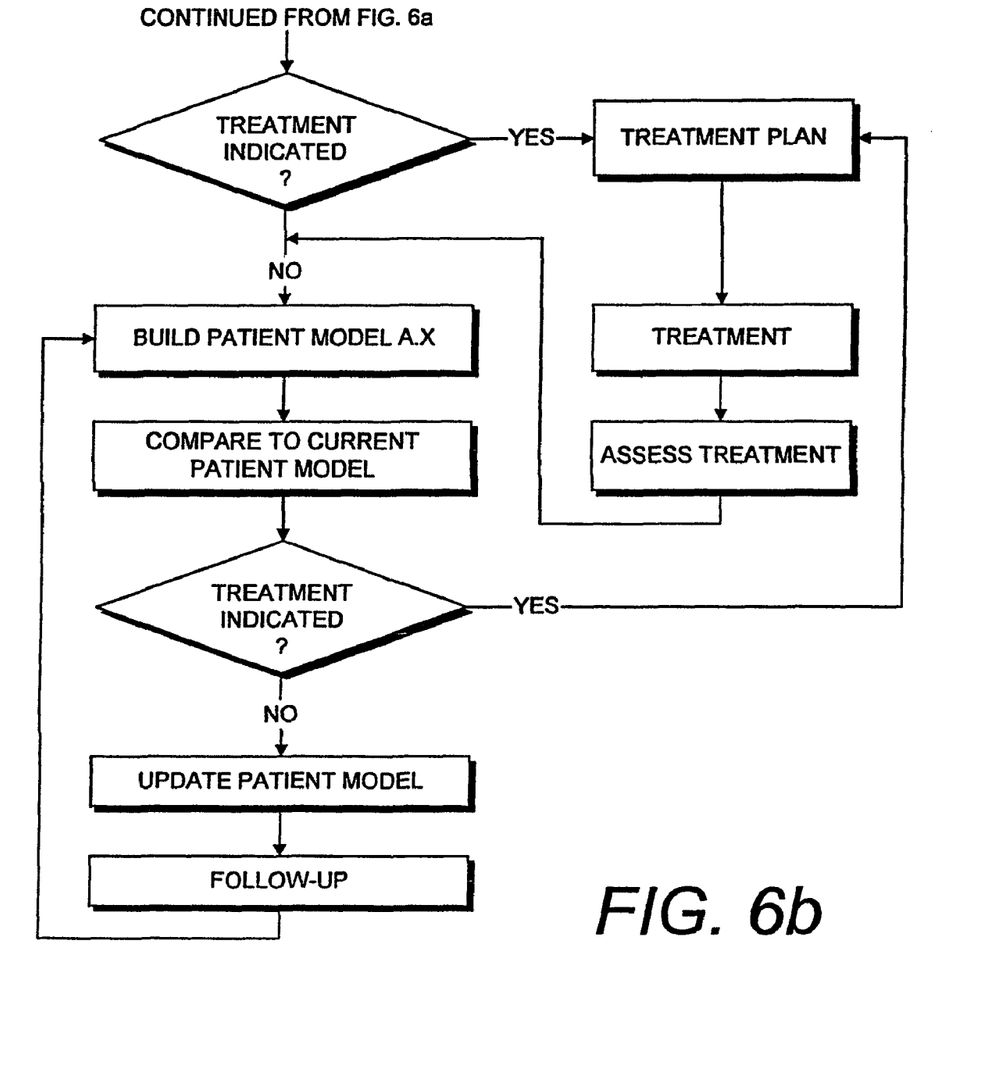

FIGS. 6a-b show a flowchart of the densitometry modeling method with respect to an individual patient. The steps of the flowchart generally correspond to routines, which can be performed either manually or with the computer 104. After starting and initializing the software, a population database/baseline is loaded. The population database/baseline can included densitometry data pertaining to the general population, or population subsets grouped by such variables and as age, gender, geographic area, etc. A predictive patient model is created from both population database information and patient-specific information, as discussed in more detail below. Examples of typical information used for creating dental models are shown, and include periapical, bite wing, whole mouth, panoramic and cephalometric densitometry data captures. Other types of data would be captured and used for creating patient models for other applications, such as orthopedic. Internal/external source/receptor selections (see FIGS. 4a-d) are made at the appropriate decision steps.

An initial patient model is created, and can be compared to a corresponding baseline model for "normal" dental/orthopedic densitometries in individuals of corresponding age, gender and other variables. The initial model can be designated A.1. If indicated, treatment can be performed.

In a follow-up session, a second model A.X can be built. The variable "X" can correspond to, for example, the version number or a time period, such as the number of days since the first model A.1 was created. The software can perform a comparison between the two patient-specific models A.1 and A.X. Densitometry changes can be noted and brought to the attention of the dentist or physician. For example, areas showing significant decreases in densitometry would alert the dentist to the possibility of incipient caries. Depending on the extent of change and compromised density, preemptive treatment might be indicated, or the area can be designated for careful future monitoring for further deterioration or change. Because certain changes are normal, the baseline, plus the patient's dental/medical history, can be utilized in distinguishing conditions requiring treatment from normal decalcification/calcification.

Implant osseointegration can also be monitored with the system and methodology of the present invention. For example, the densitometry techniques described herein can monitor the progress of a bone-implant interface, indicating successful osseointegration, whereas the continued or increased presence of soft tissue granulation would indicate a failed implant.

Other conditions that are particularly well-suited for monitoring with the system and method of the present invention include fractures, decay, abscesses, plaque and periodontal disease. Still further, 3D imaging can be provided with the system and method whereby fractures and other lesions, which are difficult to detect in 2D imaging, can be made apparent.

Figure 7:
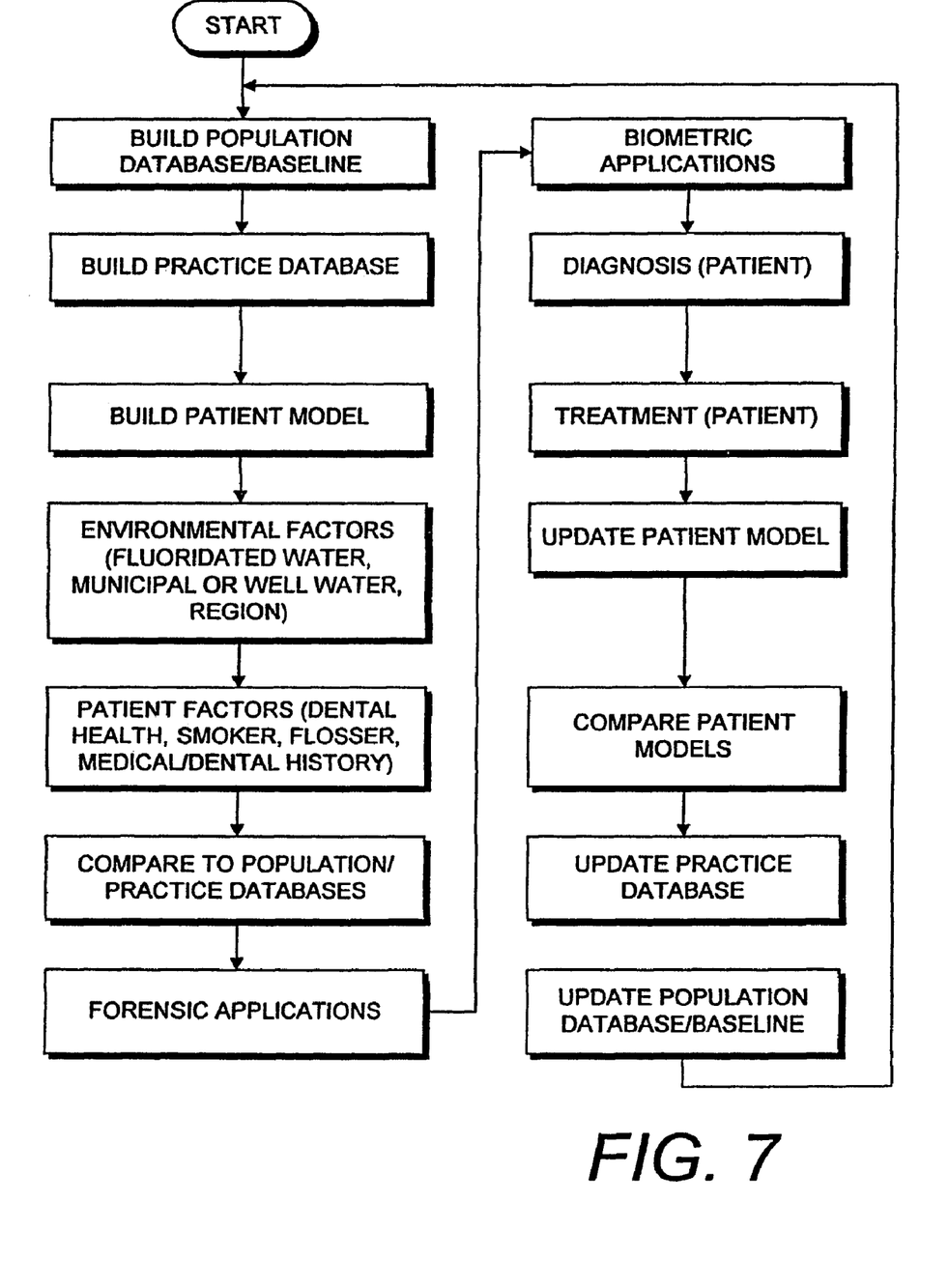
FIG. 7 is a flowchart of a general population baseline database densitometry modeling method according to the present invention.

FIG. 7 shows a flowchart for creating a baseline database, utilizing same in a dental or medical practice, and building individual patient densitometry models. As shown, the process is interactive with individual patient data being utilized in building the practice database, which in turn can be contributed to the general population baseline database. Thus, greater accuracy can be achieved in the baseline database over a period of time with contributed data from individual patients and practices. Still further, the individual patient model can be updated with each visit, and monitored against projected patient densities, as derived from the baseline.

Environmental factors, such as fluoridated, municipal or well water and geographic regional considerations can be applied as shown. Likewise, patient factors can influence the densitometry models. These include general dental health, dental hygiene (such as frequent and thorough brushing and flossing), systemic influences, oncology, zerostomia (dry mouth), transplant patients on anti-rejection medication, susceptibility to infection and decay, etc.

Additional embodiments and aspects of the method of the present invention include a number of additional applications of densitometry modeling, such as forensics, biometrics and individual identification. For example, individual identification from dental and medical records can be expedited by the digital data capture, processing, comparison and display techniques and procedures disclosed herein and adapted for use with densitometry models. In addition to the medical and dental applications, such procedures and the resulting models have applications in such fields as forensics, security (e.g., biometric identification techniques) and law enforcement.

Is to be understood that while certain aspects and embodiments of the invention are described and shown, the invention is not limited thereto and can assume a wide range of other, alternative aspects and embodiments.

What is claimed and desired to be secured by Letters Patent is as follows:

1. A dental or orthopedic densitometry modeling method, which comprises the steps of:
building an initial patient-specific densitometry model;
obtaining current densitometry data on said patient;
performing with a computer time-lapse, automated digital comparisons of said initial and current patient-specific densitometry data, said comparisons identifying dental or orthopedic densitometry changes in the dental or orthopedic structures of individual patients;
updating said initial patient-specific densitometry model;

gathering with said computer a general population baseline database of patient dental or orthopedic densitometry data including variables for age and gender;

performing with said computer automated digital comparisons of said identified dental or orthopedic densitometry changes with said general population baseline data;

building a predictive densitometry model for a patient based on information from said database;

providing an energy or field source;

providing a sensor for energy or a field emitted by said source;

placing said source and sensor on opposite sides of a patient's dental or orthopedic structure to be modeled;

emitting energy or a field from said source, passing same through said patient's structure; and sensing said energy or field with said sensor;

identifying a localized dental or orthopedic structure area as a watch area based on densitometry model changes with respect to the patient;

directing said energy or field source towards the localized dental or orthopedic structure watch area; and obtaining specific, localized densitometry information concerning the densitometry model of said area.

2. The method according to claim 1, which includes the additional steps of:

including in said patient-specific densitometry model dental densitometry information obtained from a dental examination of one or more the following areas:

periapical, bite wing, whole mouth, panoramic or cephalometric.

3. The method according to claim 1 wherein said source is a hand-held CRT.

4. The method according to claim 1, which includes the additional step of:

converting a former procedure using subjective or analog information in a dental or medical office to the use of digital densitometry data.

* * * * *